(12) United States Patent
Mace et al.

(10) Patent No.: US 9,597,577 B2
(45) Date of Patent: Mar. 21, 2017

(54) METHOD FOR PROCESSING DATA REPRESENTATIVE OF PERFORMANCES OF A TENNIS PLAYER

(71) Applicants: Pierre Mace, Lyons (FR); Fabien Gauthier, Lyons (FR)

(72) Inventors: Pierre Mace, Lyons (FR); Fabien Gauthier, Lyons (FR)

(73) Assignee: BABOLAT VS, Lyons (FR)

( * ) Notice: Subject to any disclaimer, the term of this patent is extended or adjusted under 35 U.S.C. 154(b) by 202 days.

(21) Appl. No.: 14/460,775

(22) Filed: Aug. 15, 2014

(65) Prior Publication Data

US 2015/0057777 A1 Feb. 26, 2015

(30) Foreign Application Priority Data

Aug. 21, 2013 (FR) ..................... 13 58106

(51) Int. Cl.
| | |
|---|---|
| *A63F 9/24* | (2006.01) |
| *A63B 69/38* | (2006.01) |
| *G06F 19/00* | (2011.01) |
| *A63B 24/00* | (2006.01) |
| *A63B 71/06* | (2006.01) |

(52) U.S. Cl.
CPC .......... *A63B 69/38* (2013.01); *A63B 24/0003* (2013.01); *A63B 24/0062* (2013.01); *A63B 71/0619* (2013.01); *G06F 19/3481* (2013.01); *A63B 2024/0065* (2013.01); *A63B 2024/0068* (2013.01); *A63B 2220/17* (2013.01)

(58) Field of Classification Search
CPC ..... G06F 3/0481; G06T 11/206; A63B 69/38; G06Q 10/0639
See application file for complete search history.

(56) References Cited

U.S. PATENT DOCUMENTS

| | | |
|---|---|---|
| 2011/0183787 A1 | 7/2011 | Schwenger et al. |
| 2013/0053190 A1 | 2/2013 | Mettler |

FOREIGN PATENT DOCUMENTS

| | | | |
|---|---|---|---|
| CH | 705 403 A1 | 2/2013 | |

OTHER PUBLICATIONS

FR Search Report, dated Jul. 2, 2014, from corresponding FR application.

*Primary Examiner* — Reginald Renwick
(74) *Attorney, Agent, or Firm* — Young & Thompson

(57) ABSTRACT

A method of processing data representing the performance of a tennis player in a display device includes: a) calculating, using data including physical quantities measured during a game period including one or several game sessions and transferred into a system for calculating of the display device, at least three parameters representing the player's performance during this game period, b) displaying, in the form of a diagram including one axis for each parameter, with the axes forming a star with several branches, points corresponding to the values of the parameters on the axes so as to form a generally polygon-shaped closed contour encompassing or passing through the points, and c) alternatively increasing and decreasing the surface area delimited by the closed contour according to a frequency of the variation calculated according to the effective game time of the player measured during the last game session of the game period.

15 Claims, 3 Drawing Sheets

METHOD FOR PROCESSING DATA REPRESENTATIVE OF PERFORMANCES OF A TENNIS PLAYER

FIELD OF THE INVENTION

The invention relates to a method for processing data representing the performance of a tennis player on a display device.

BACKGROUND OF THE INVENTION

In the practice of tennis, it is useful to have a means of viewing the change in the performance of a player over time, in particular with a portable display device, such as a mobile telephone, a tablet or a portable computer. Sensors installed in the racket make it possible to measure a certain number of parameters, in particular the number of strokes and the characteristics of these strokes, and to transfer them into a portable display device. However, the performance of a player can be represented in many ways and using multiples indexes, which makes clear and summarised viewing difficult.

SUMMARY OF THE INVENTION

The object of the invention proposes a new method of processing data representing the performance of a tennis player making it possible to view, via particular processing and display techniques, a certain number of parameters thanks to which the player or those around him can have a general overview of his performance.

To this effect, the invention relates to a method for processing data representing the performance of a tennis player via a display device, characterised in that it comprises steps consisting in:

a) calculating, using data comprising physical quantities measured during a game period comprising one or several game sessions and transferred into a system for calculating of the display device, at least three parameters representing the performance of the player during this game period, b) displaying, in the form of a diagram comprising one axis for each parameter, with the axes forming a star with several branches, points corresponding to the values of the parameters on the axes in such a way as to form a generally polygon-shaped closed contour encompassing or passing through said points, c) alternatively increasing and decreasing the surface area delimited by the closed contour according to a frequency of the variation calculated according to the effective game time of the player measured during the last game session of the game period.

Thanks to the invention, a tennis player can quickly view, thanks to glancing on a screen of his display device, an overview of his performance based on at least three parameters and to assess the pertinence of them thanks to variations in the surface area delimited by the closed contour, which reflects the game frequency of the player.

According to advantageous but not mandatory characteristics of the invention, such a method can incorporate one or several of the following characteristics, taken in any technically permissible combination:

The method comprises additional steps consisting in:

d) determining, for each stroke carried out during the game period, the type of this stroke from among a predefined list of types of strokes that comprises at least two types of strokes, e) recording, for each type of stroke on the list of strokes, the total number of strokes carried out;

f) colouring a surface delimited by the closed contour in a colour that represents the level of the player, with this level being determined according to the total number of strokes carried out for each type of stroke on the list of types of strokes.

The list of types of strokes comprises at least four types of strokes, among which the forehand, the backhand, the serve and the smash.

The method comprises a step consisting in reporting the reaching by the player of a predefined number of strokes for each type of stroke via a change in the colour of the surface delimited by the closed contour and the adopting of a shade corresponding to a higher level in relation to the level wherein the player was before reaching the predefined numbers of strokes for each type of stroke.

The parameters calculated in the step a) are respectively representative of the power developed by the player during the game period, of the endurance of the player during the game period and of the technical skills of the player during the game period, and the closed contour has a generally triangular shape.

The frequency of the variation of the surface area delimited by the closed contour is limited to a maximum value which is reached when the effective game time during the last game session of the game period reaches a threshold value.

The frequency of the variation of the surface area delimited by the closed contour decreases when the player does not transfer any data for a predetermined period of time.

When frequency of the variation becomes zero, the total numbers of strokes for each type of stroke starts to decrease.

Every time data concerning a new game session is transferred by the player into the display device, the variations in the surface area of the closed contour are extended for a period of time calculated according to the effective game time measured during this last game session.

The method comprises a step consisting in calculating an average value of at least three parameters calculated in the step a) and a step consisting in comparing, by means of a data network, the performance of different tennis players based on this average value.

BRIEF DESCRIPTION OF THE DRAWINGS

The invention shall be better understood and other advantages of the latter shall appear more clearly when reading the following description of a method in accordance with its principle, given by way of a non-restricted example in reference to the annexed drawings wherein.

Figure 1:
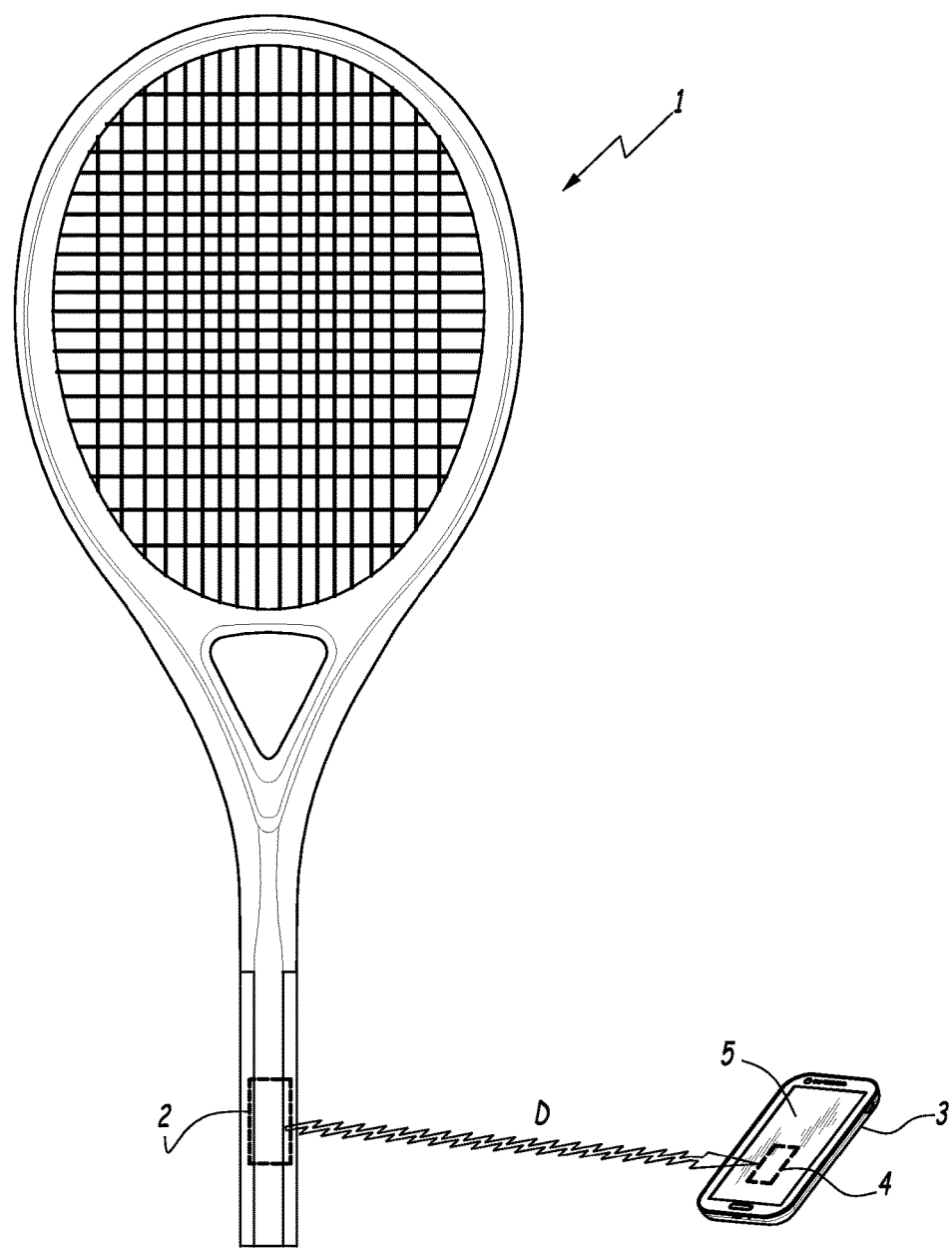
FIG. 1 is a diagrammatical view of a tennis racket and of a display device allowing for the implementation of the method in accordance with the invention.

The method of the invention is implemented with a tennis racket 1 provided with a system 2 for measuring game data D. The system for measuring 2 comprises sensors not shown able to measure, during the hitting of a ball with the racquet 1, data D including physical quantities such as the linear acceleration and the angular speed of the racket 1 according to three directions perpendicular to each other and fixed in relation to a terrestrial reference. For example, the system for measuring 2 can comprise a triple-axis accelerometer and a triple-axis gyrometer.

During a game period comprising several game sessions, game data D are measured, in a first step 100 of the method according to the invention, by the system for measuring 2 when a player carries out series of strokes (forehand topspin stroke, serve, backhand slice, etc.).

When the player finishes a game session, he connects his racquet 1 to a display device 3, such as a computer, a tablet or a mobile telephone, in such a way as to transfer, in a step 101, the data D collected in the step 100, into the display device which, in the example shown, is a mobile telephone 3.

The connection between the display device 3 and the racquet 1 can be carried out by the intermediary of a wired connection, for example of the USB type, or a wireless connection, for example of the Bluetooth type.

The display device 3 comprises a built-in system for calculating 4 able to automatically calculate, in a step 102, and using data D transferred in the step 101, three parameters representing the performance of the player. These three parameters can be, for example, a parameter P1 representing the power developed by the player during the last game session, a parameter P2 representing the endurance of the player during the game period, and a parameter P3 representing the technical skills of the player, based on the regularity and the variety of the strokes carried out during the game period.

In a step 103, based on the values of the parameters P1, P2 and P3, the method automatically displays, on a screen 5 of the display device 3, the three parameters on a diagram comprising three axes that form a star with three branches, with each axis corresponding to one of the parameters P1, P2 and P3. The respective values V1, V2 and V3 of the parameters P1, P2 and P3 are represented on the axes P1, P2 and P3 by points V1, V2 and V3.

The three points V1, V2 and V3 define a closed contour A with a generally triangular shape which encompasses or passes through the points V1, V2, and V3. The term "generally triangular shape" means that the closed contour A generally has three extended portions extending respectively between the points V1 and V2, between the points V1 and V3 and between the points V2 and V3 and which form angles between them.

Figure 2:
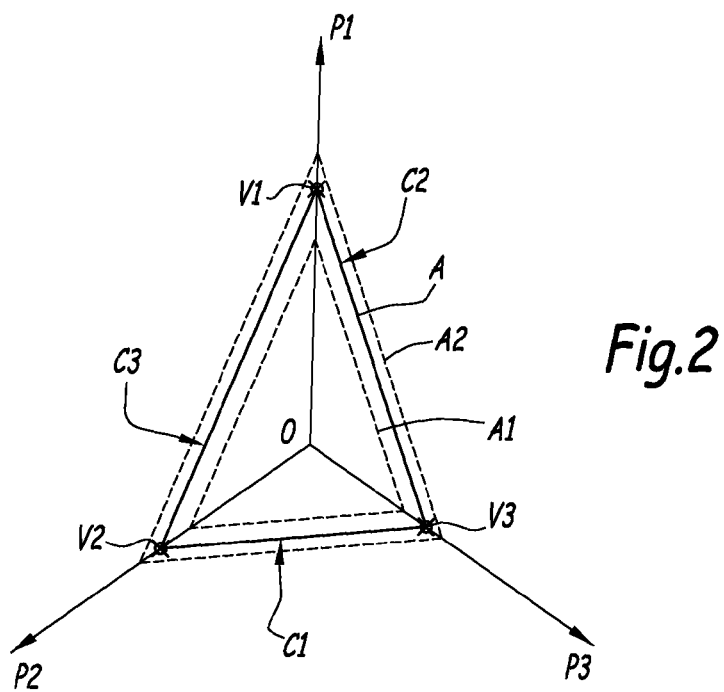
FIG. 2 shows a display obtained by a first embodiment of the method in accordance with the invention.

In a first embodiment shown in FIG. 2, the closed contour A forms a triangle in the geometrical sense of the term. The points V1, V2 and V3 are connected by sides C1, C2 and C3 formed by straight segments. In an alternative not shown, the sides C1, C2 and C3 can pass around points V1, V2 and V3.

Figure 3:
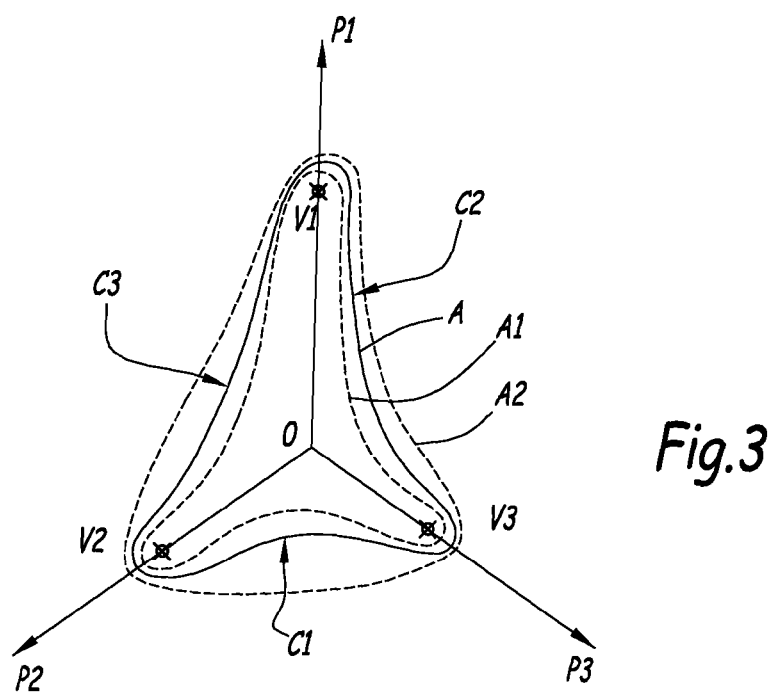
FIG. 3 shows a display obtained by a second embodiment of the method in accordance with the invention.
Figure 4:
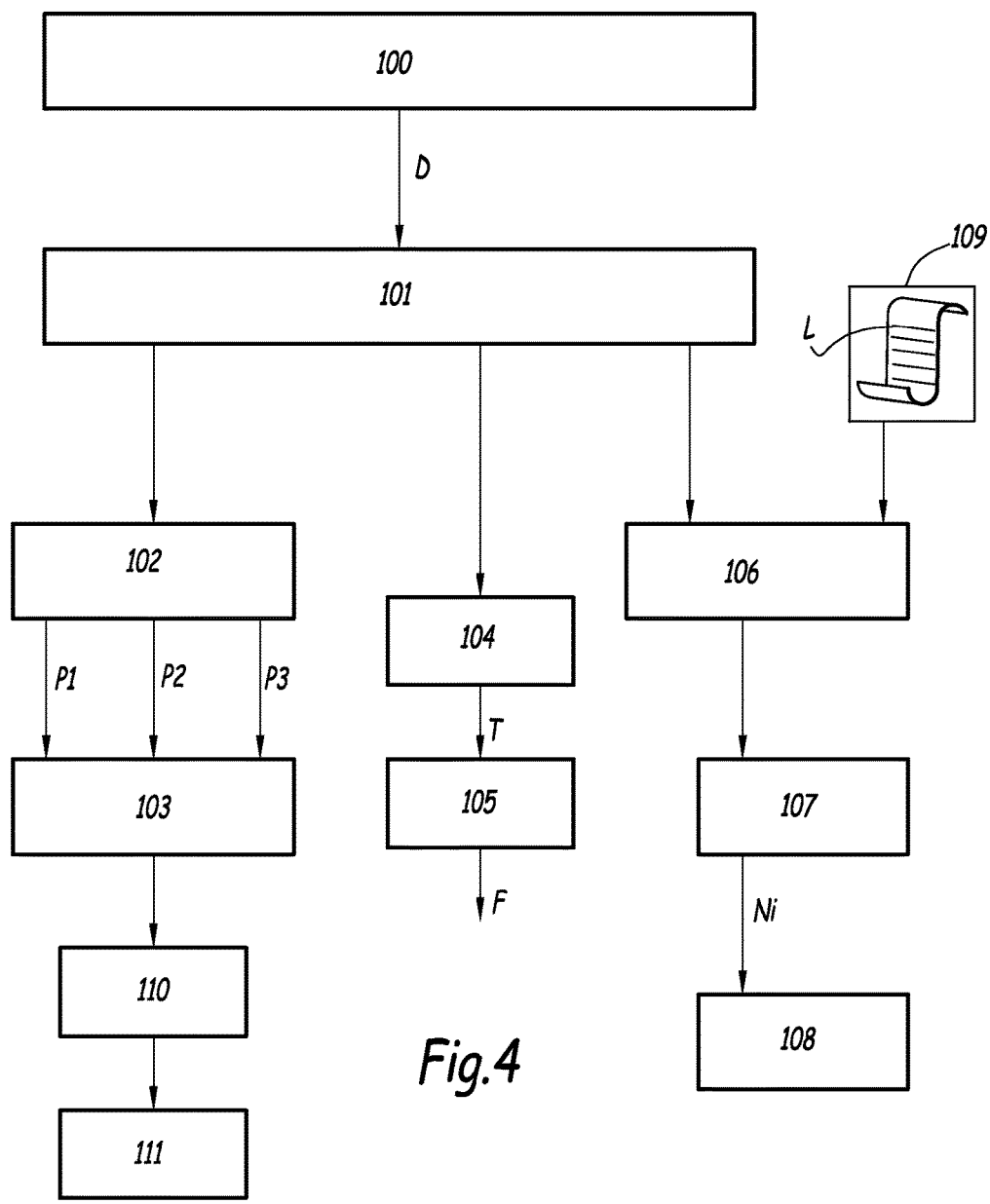
FIG. 4 is a block diagram of the method in accordance with the invention.

In a second embodiment shown in FIG. 3, the closed contour A comprises three curved lines C1 and C2 and C3 extending between the points V1, V2 and V3, and connected together two-by-two around points V1, V2 and V3. In an alternative not shown, the curves C1, C2 and C3 can also pass through the points V1, V2 and V3.

In a step 104, which can be simultaneous to the step 102, the effective game time T of the tennis player over the last game session is calculated using data D transferred in the step 101. The effective game time T is calculated, during the data acquisition by the system for measuring 2, by measuring the interval of time that separates each stroke executed by the player. When this interval of time is greater than a predetermined duration, indicating that the player is no longer effectively hitting strokes, this interval of time is not considered as effective game time and is not taken into account.

According to the measurement of the effective game time T carried out in the step 104, the closed contour A shown in the step 103 is modified in a step 105 in order to alternatively increase and decrease the surface area that it delimits according to a predetermined frequency of the variation F. The frequency of the variation F is called in what follows "beat frequency". The surface area of the closed contour A varies between a minimum surface area delimited by a contour A1 and a maximum surface area delimited by a contour A2.

In the first embodiment shown in FIG. 2, the variations in surface area are obtained by increasing and by decreasing the length of the sides C1, C2 and C3, by carrying out scalings of the closed contour A.

In the second embodiment shown in FIG. 3, the variations in surface area of the closed contour A are obtained by modifying the curvature of the curves C1, C2 and C3 and/or by modifying the total length of the closed contour A, in particular in the vicinity of the points V1, V2 and V3.

The various ways of displaying the closed contour A and of varying the surface area that it delimits can be combined together in the scope of the invention. It is for example possible to display the closed contour A in the form of a triangle of which the apices are the points V1, V2 and V3, and to modify its surface area by transforming its rectilinear sides C1, C2 and C3 into curved lines that have variable radii of curvature.

The beat frequency F of the closed contour A is limited to a maximum value $F_0$, for example 150 beats per minute, which corresponds to 150 surface area variations per minute.

The maximum beat frequency $F_0$ of the closed contour A is reached when the last game session of which the data D is transferred comprises a maximum effective game time that is greater than a predetermined value $\Delta T1$, for example forty minutes. This means that for example, if the player transfers a game session of one hour, corresponding to forty-five minutes of effective game T, the effective game time taken into account is forty minutes and triggers a "beat" of the closed contour A at 150 beats per minute.

The "beat" of the closed contour A has a duration that is limited over time. If the player does not provide new data D for a certain period of time $\Delta T2$ after the last transfer of data, for example one week, the beat frequency F decreases to a predetermined value, for example 110 beats per minute. If after another period of time $\Delta T3$, for example one week, the player has still not transferred new data D into the system for calculating 4, the beat frequency F falls to zero.

The timeframes starting from which the beat frequency F starts to decrease and the number of stages used can be different.

If the beat frequency F of the closed contour A is equal to a value less than the maximum value, transferring a game session that comprises an effective game time T that is not zero but less than forty minutes makes it possible to increase the beat frequency F for a certain period of time. For example, an effective game time T of ten minutes can extend the period during which the closed contour A will "beat" for a period of time $\Delta T4$ equal to four days. If at the time when these ten minutes of game are taken into account by the system for calculating, the beat frequency F is equal to 50 beats per minute, the taking into account of this new quantity of effective game time T also makes it possible to increase the beat frequency F to 100 battements par minutes, by way of example.

In a step 106 which takes place after the step 101 and which can be simultaneous to the steps 102 to 105, each stroke carried out by the player during the game period is classed in a type of stroke defined among a list L of the types of strokes comprising at least two types of strokes. In this example, the list L of types of strokes comprises four types of strokes, this number including the forehand, the backhand, the serve and the smash. Alternatively, the list L of the types of strokes can comprise more than four strokes. The variable i is assigned to each type of stroke, i being between 1 and 4.

Optionally, the method can include a step 109 that takes place before the step 106 and which consists in choosing the types of strokes of the list L of types of strokes.

In a step 107, over a given game period, the system for calculating 4 determines the number of strokes Ni executed for each type of stroke i by adding, during each data transfer in the step 101, the numbers of strokes of each type of stroke played during each game session of which the data is transferred. As such, the system for calculating 4 comprises for each one of the four types of strokes i of the list L of strokes, the total number of strokes Ni carried out by the player since his first use of the racquet.

In a step 108, using the numbers of strokes Ni calculated in the step 106, a game level of the player is determined. In order to obtain this level, the player must have carried out a predetermined number of strokes in each type of stroke. Initially, the player is at the zero level and moves towards the level 1 once he has carried out, for example, a number CD1 of forehands, a number RE1 of backhands, a number SE1 of serves and a number SM1 of smashes. For example, the numbers CD1, RE1, SE1 and SM1 are respectively equal to 200, 200, 50 and 5. In order to move to level 2, the player must carry out a number CD2, for example 500, of forehands, a number RE2, for example 400 of backhands, a number SE2, for example 100, of serves and a number SM2, for example 20, of smashes. Moving to each higher level is conditioned by the execution of a predetermined number of strokes for each type of stroke.

In order to show the level of the player on the diagram of the display device 3, the surface delimited by the closed contour A is coloured with a predetermined colour shade. For example, the level 0 is represented by the colour dark blue.

Each time the player reaches, for each type of stroke i, the number of strokes CD1, CD2, etc., RE1, RE2, etc., SE1, SE2, etc., SM1, SM2, etc. required to access the higher level, exceeding the numbers of strokes triggers the change in the shade of the colour of the surface delimited by the closed contour A in order to adopt the colour corresponding to the higher level. The predefined number of strokes for each type of stroke required to move to the higher level is increased to new values.

If a player classed in a certain level has carried out enough strokes i in one or in several types of strokes i, but has not executed enough strokes in at least one other type of stroke, he cannot move to the higher level.

By way of example, the system for calculating 4 can be configured in such a way that seven levels can be reached. In this case, seven different colours are provided for the surface area of the surface delimited by the contour A. As such, a quick glance at the screen 5 allows the player to know his level.

When the beat frequency F of the closed contour A decreases until it reaches zero, the numbers of strokes Ni for each type of strokes i accumulated by the player also start to decrease. The more time T' elapses since the arrival of the beat frequency F at zero increases without data D being transferred, the more the player loses a substantial number of hits for each type of stroke. By way of example, after one week after the arrival of the beat frequency at zero, the player can lose 25% of the strokes accumulated in each type of stroke. As such, his level can decrease if he does not play during a period $\Delta T5$ equal, in the example, to one week.

According to an optional aspect, the system for calculating 4 can warn the player a certain period of time, for example one day, before the beat frequency reaches the zero value, for example via a message that is displayed on the screen 5 of the display device 3.

According to another optional aspect of the invention, the display device 3 can be connected to a network such as Internet, so that different players can compare their performance. Preferably, the average of the values of the three parameters P1, P2 and P3 is calculated, in the display device 3 or in another system, in particular with an internet site, during a step 110. Then, the average values calculated in the step 110 are compared with each other in a step 111 in order to classer the players in relation to one another according to their performance. The step 111 is preferably carried out on an internet site to which the players connect and on which they can transfer the data pertaining to them.

Alternatively, the comparisons between players can also be made using the numbers of strokes Ni in each type of stroke i, levels, or beat frequencies F of the closed contour A of the different players.

According to an embodiment not shown of the invention, the method of processing is able to calculate more than three parameters representing the performance of a player. In addition to the parameters P1, P2 and P3, the system for calculating 4 can in particular calculate parameters that represent, for example the strategy level of the player, his level of aggressiveness, or his mental level. In such a case, the shape of the closed contour A displayed in the step 103 is generally polygonal and the diagram comprises as many axes as parameters calculated in the step 102.

The characteristics of the various embodiments and alternatives described hereinabove can be combined in order to generate new embodiments of the invention.

The invention claimed is:

1. A method for representing the performance of a tennis player, the method comprising the steps of:
   a) the tennis player carrying out a series of strokes hitting a ball with a racquet comprising an integrated system for measuring game data, the system for measuring game data comprising sensors configured to measure the game data, the game data measured by the sensors comprising physical quantities including linear acceleration and angular speed of the racquet during the strokes;
   b) measuring, in each series of the strokes, game data using the system for measuring game data provided in the racquet, wherein the measured game data comprises the physical quantities including linear acceleration and angular speed of the racquet during the strokes;
   c) calculating, using the game data comprising the physical quantities measured at step b), during a game period comprising one or several game sessions, said each game sessions comprising series of strokes carried at step a), and transferred from the system for measuring game data into a system for calculating of a display device, at least three parameters representing the performance of the player during the game period, said parameters being chosen between at least a parameter representative of the power developed by the player during the game period, a parameter representative of the endurance of the player during the game period and a parameter representative of the technical skills of the player during the game period, d) displaying on the display device, in the form of a diagram comprising one axis for each parameter calculated at step c), with the axes forming a star with several branches, points corresponding to values of the parameters on the axes in such a way as to form a generally polygon-shaped closed contour encompassing or passing through said points, e) alternatively increasing and decreasing a surface area delimited by the closed contour according to a frequency of the variation calculated according to the effective game time of the player measured during the last game session of the game period.

2. The method according to claim 1, comprising the additional steps of:

f) determining, using the game data measured at step b), for each stroke carried out during the game period, the type of stroke among a predefined list of types of strokes comprising at least two types of strokes chosen among at least the forehand, the backhand, the serve and the smash, g) recording, for each type of stroke on the list of strokes, the total number of strokes carried out;

h) colouring a surface delimited by the closed contour in a colour that represents the level of the player, with this level being determined according to the total number of strokes carried out for each type of stroke on the list of types of strokes.

3. The method according to claim 2, further comprising a step of reporting the reaching by the player of a predefined number of strokes for each type of stroke via a change in the colour of the surface delimited by the closed contour and the adopting of a shade corresponding to a higher level in relation to the level wherein the player was before reaching the predefined numbers of strokes for each type of stroke.

4. The method according to claim 1, wherein the closed contour (A) has a generally triangular shape.

5. The method according to claim 1, wherein the frequency of the variation of the surface area delimited by the closed contour is limited to a maximum value which is reached when the effective game time during the last game session of the game period reaches a threshold value.

6. The method according to claim 2, wherein the frequency of the variation of the surface area delimited by the closed contour decreases when the player does not transfer data for a predetermined period of time.

7. The method according to claim 6, wherein when the frequency of the variation becomes zero, the total numbers of strokes for each type of stroke start to decrease.

8. The method according to claim 1, wherein, each time data concerning a new game session is transferred by the player into the display device, the variations in the surface area of the closed contour are extended for a period of time calculated according to the effective game time measured during this last game session.

9. The method according to claim 1, further comprising a step of calculating an average value of the at least three parameters calculated in the step a) and a step consisting in comparing, by means of a data network, the performance of different tennis players based on the average value.

10. The method according to claim 1, wherein the frequency of the variation of the surface area delimited by the closed contour decreases when the player does not transfer data for a predetermined period of time.

11. The method according to claim 1, wherein step c) further includes transferring the game data from the system for measuring game data into a system for calculating of the display device by connecting the display device to the system for measuring game data of the racquet using one of the group consisting of i) a wired connection, and ii) a wireless connection.

12. A method representing the performance of a tennis player on a display device, the method comprising the steps of:

a) the tennis player carrying a series of strokes hitting a ball with a racquet, the racquet comprising an integrated system for measuring game data, the system for measuring game data comprising sensors, including a triple-axis accelerometer and a triple-axis gyrometer, the sensors configured to measure the game data comprising physical quantities including linear acceleration and angular speed of the racquet according to three directions perpendicular to each other and fixed in relation to a terrestrial reference;

b) measuring, in each series of the strokes, the game data using the system for measuring game data provided in the racquet, wherein the measured game data comprises the physical quantities including linear acceleration and angular speed of the racquet during the strokes;

c) calculating at least three parameters using the sub-steps of:

c1) connecting the racquet to the display device, the display device being a portable display device comprised of a system for calculating performance parameters, c2) transferring the game data from the system for measuring game data into the system for calculating performance parameters of the display device, and c3) the system for calculating performance parameters using the transferred game data comprising physical quantities measured at step b) during a game period comprising at least one game session comprising the series of strokes carried at step a), to automatically calculate at least three parameters representing the performance of the player during the game period, said parameters including at least a parameter representative of the power developed by the player during the game period, a parameter representative of the endurance of the player during the game period, and a parameter representative of the technical skills of the player during the game period, wherein the connecting of the racquet to the display device is performed using one of the group consisting of i) a wired connection, and ii) a wireless connection;

d) displaying on the display device a diagram comprising one axis for each parameter calculated at step c), with the axes forming a star with plural branches, points corresponding to values of the parameters on the axes to form a generally polygon-shaped closed contour encompassing or passing through said points; and e) alternatively increasing and decreasing a surface area delimited by the closed contour according to a frequency of the variation calculated according to the effective game time of the player measured during a last game session of the game period.

13. The method for processing according to claim 12, further comprising the steps of:

f) determining, using the game data measured at step b), for each stroke carried out during the game period, the type of stroke among a predefined list of types of strokes comprising at least two types of strokes chosen among at least the forehand, the backhand, the serve and the smash;

g) recording, for each type of stroke on the list of strokes, the total number of strokes carried out; and h) colouring a surface delimited by the closed contour in a colour that represents the level of the player, with this level being determined according to the total number of strokes carried out for each type of stroke on the list of types of strokes.

14. The method for processing according to claim 12, wherein the display device is one of the group consisting of a mobile telephone, a tablet, and a portable computer.

15. The method for processing according to claim 14, wherein the connecting of the racquet to the display device is performed a Bluetooth wireless connection.

* * * * *